US010925913B2

(12) United States Patent
Liu et al.

(10) Patent No.: US 10,925,913 B2
(45) Date of Patent: Feb. 23, 2021

(54) LOW TOXIC TRIPTERYGIUM NEOGLYCOSIDES, PREPARATION METHOD AND APPLICATION THEREOF

(71) Applicants: THE SECOND AFFILIATED HOSPITAL OF GUANGZHOU UNIVERSITY OF CHINESE MEDICINE, Guangdong (CN); GUANGZHOU UNIVERSITY OF CHINESE MEDICINE, Guangzhou (CN)

(72) Inventors: Bo Liu, Guangdong (CN); Wei Mao, Guangdong (CN); Xusheng Liu, Guangdong (CN); Peng Xu, Guangdong (CN); Xiaodong Han, Guangdong (CN); Wen Zhou, Guangdong (CN); Fangfang Xu, Guangdong (CN); Yuanchao Li, Guangdong (CN); Yiqi Yang, Guangdong (CN); Jinbao Deng, Guangdong (CN); Lilan Wu, Guangdong (CN); Yunshan Wu, Guangdong (CN); Weiying Chen, Guangdong (CN); Ruimin Tian, Guangdong (CN); Jinjian Lu, Guangdong (CN); Yuqin Zhang, Guangdong (CN)

(73) Assignees: THE SECOND AFFILIATED HOSPITAL OF GUANGZHOU UNIVERSITY OF CHINESE MEDICINE, Guangzhou (CN); GUANGZHOU UNIVERSITY OF CHINESE MEDICINE, Guangzhou (CN)

( * ) Notice: Subject to any disclaimer, the term of this patent is extended or adjusted under 35 U.S.C. 154(b) by 0 days.

(21) Appl. No.: 16/492,725

(22) PCT Filed: Aug. 30, 2017

(86) PCT No.: PCT/CN2017/099589
§ 371 (c)(1),
(2) Date: Sep. 10, 2019

(87) PCT Pub. No.: WO2018/161507
PCT Pub. Date: Sep. 13, 2018

(65) Prior Publication Data
US 2020/0069757 A1 Mar. 5, 2020

(30) Foreign Application Priority Data

Mar. 10, 2017 (CN) .......................... 201710142189.1

(51) Int. Cl.
A61K 36/00 (2006.01)
A61K 36/37 (2006.01)
(52) U.S. Cl.
CPC ........ A61K 36/37 (2013.01); A61K 2236/333 (2013.01)
(58) Field of Classification Search
None
See application file for complete search history.

(56) References Cited

FOREIGN PATENT DOCUMENTS

| CN | 101708193 A | * | 5/2010 |
| CN | 101991633 A | | 3/2011 |
| CN | 106860500 A | | 6/2017 |

OTHER PUBLICATIONS

Bai, Jie. Investigation of the Separation and Modification Methods of the Active Components in Tripergium Wilfordii Hook.F. Chinese Doctoral Dissertations & Master's Theses Full-text Databases (Master), Engineering Science and Technology I, Dec. 15, 2005 (Dec. 15, 2005), No. 8, B016-137, the abstract, and pp. 21-26.
International Search Report dated Dec. 14, 2017 from corresponding PCT Application No. PCT/CN2017/099589.
Li, Tong. Extract Polyglycosides from Tripterginum Wilfordii Hook. F and its Micronization. Chinese Master's Theses Full-text Database, Medicine and Health Sciences, Mar. 15, 2011 (Mar. 15, 2011), No. 3, E057-44, pp. 7 and 29.

* cited by examiner

Primary Examiner — Qiuwen Mi
(74) Attorney, Agent, or Firm — Innovation Capital Law Group, LLP; Vic Lin

(57) ABSTRACT

The disclosure relates to a low toxic *tripterygium* neoglycosides, which is obtained by chemically processing *tripterygium* glycosides and adding triptriolide. The disclosure also discloses the application of the low toxic *tripterygium* neoglycosides. The *tripterygium* neoglycosides can effectively relieve renal pathological injury and urinary protein of nephrotic syndrome, attenuate the inflammatory level of the body, have obvious treatment effect on nephrotic syndrome, and have low toxicity and persistent effect.

1 Claim, 9 Drawing Sheets

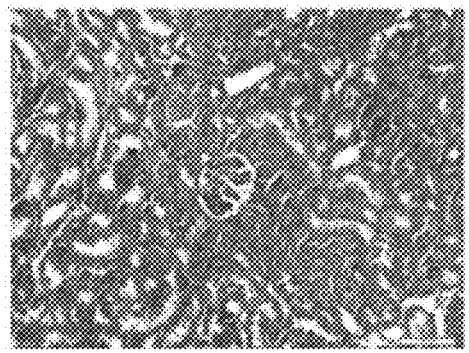
A Optical microscope graph of kidney tissue of blank group

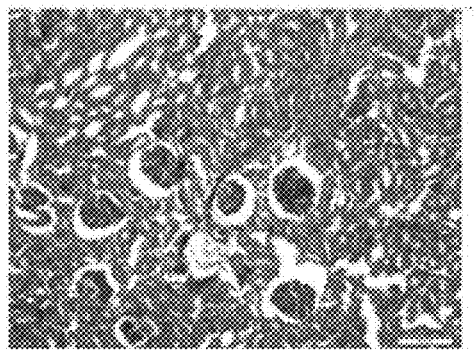
B Optical microscope graph of kidney tissue of model group

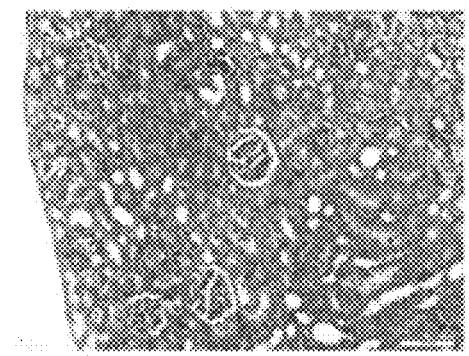
C Optical microscope graph of kidney tissue of glycoside group

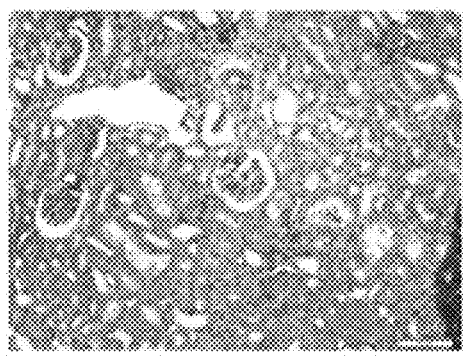
D Optical microscope graph of kidney tissue of neoglycosides I group

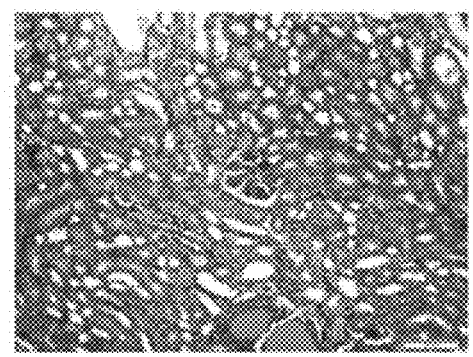
E Optical microscope graph of kidney tissue of neoglycosides II group

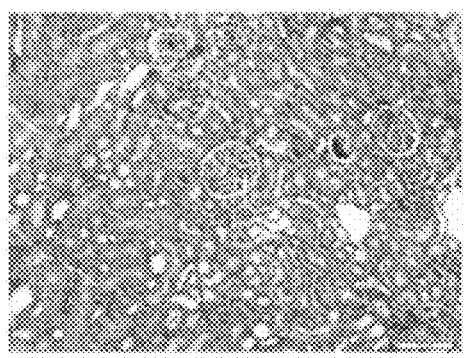
F Optical microscope graph of kidney tissue of neoglycosides III group

Fig.15

LOW TOXIC TRIPTERYGIUM NEOGLYCOSIDES, PREPARATION METHOD AND APPLICATION THEREOF

FIELD

The disclosure relates to the field of medicine and drug, in particular to a low toxic *tripterygium* neoglycosides, its preparation method and medical application thereof.

BACKGROUND

*Tripterygium* glycosides are a group of mixed glycosides extracted from the root, bark and leaf of *Tripterygium wilfordii* Hook. f. of Celastraceae. The main chemical components of *tripterygium* glycosides comprise diterpene lactone, alkaloid, and triterpene, etc. Pharmacological studies have proved that *tripterygium* glycosides have anti-inflammatory, immunosuppressive or immunoregulatory, anti-tumor and other effects. It is a hot research topic as an immunomodulatory drug in the whole world. It can be used to treat rheumatoid arthritis, primary glomerular nephropathy, nephrotic syndrome, purpuric and lupus nephritis, lupus erythematosus, subacute and chronic severe hepatitis, and chronic active hepatitis. It can also be used for allergic skin vasculitis, dermatitis, eczema, psoriatic arthritis, leprosy reaction, Behcet's disease, recurrent aphtha, and ankylosing spondylitis, etc.

Since *tripterygium* glycosides were used in clinic, adverse reactions occur from time to time, involving the blood, reproductive system, urinary system and digestive system. On one hand, the main effective components of *tripterygium* glycosides, diterpenoid components such as triptolide, triptonide, etc., triterpenoid components such as Celastrol, wilforllide A, triptolide, etc., and alkaloids such as wilforgine, wilforine, etc. have great toxicity. On the other hand, the quality of standard or proportional extracts of *tripterygium* glycosides on the market often was controlled by using triptolide as a single marker, resulting in the existing of various *tripterygium* glycosides extracts.

As early as 1991, Ma Pengcheng, et al. first isolated and identified the structure of triptriolide. However, the content of triptriolide in the plants is extremely low, and only 720 mg of triptriolide can be obtained from 20 kg of *Tripterygium wilfordii* Hook. f. In the same year, Zheng Jiarun, et al. also studied triptriolide in a relief experiment and serum in blood volume determination experiment on rat with ear swelling model. The results showed that triptriolide had weak anti-inflammatory activity but no immunosuppressive activity. Therefore, triptriolide has not been widely investigated in the field of drug research.

SUMMARY

The disclosure aims at providing a brand-new and low toxic *tripterygium* glycosides which named as *tripterygium* neoglycosides.

A further object of the disclosure is to provide a preparation method of the *tripterygium* neoglycosides.

A further object of the disclosure is to provide an application of the *tripterygium* neoglycosides in pharmacy.

According to one aspect of the disclosure, the disclosure provides a low toxic *tripterygium* neoglycosides, which is prepared by the following method:

(1) In a buffer solution prepared by sodium dihydrogen phosphate and phosphoric acid with a pH of 3.0-5.0, *tripterygium* glycosides (save some sample for triptolide detection) are heated to reflux for hydrolysis reaction for 18-96 h (preferably 30 h) in an oil bath at 90-120° C.

After the reaction is completed, the solvent is removed under reduced pressure (or by extraction). The residue was redissolved in anhydrous ethanol, centrifuge. Insoluble substances were removed. Quantitively transfer some filtrate to volumetric flask and anhydrous ethanol was added to volume, HPLC analysis to calculate the amount of triptolide in the sample and the reduction amount of triptolide in the hydrolyzed product.

(2) Triptriolide-anhydrous ethanol solution was added to the reaction product in step (1), mixed and, the solvent was removed to obtain low toxic *tripterygium* neoglycosides; the amount of triptriolide added was 0-20 times of the reduction amount of the triptolide in molar ratio.

Anhydrous ethanol in steps (1) and (2) can also be replaced by other nontoxic organic solvents, such as isopropanol.

The *tripterygium* glycosides are prepared by the following method:

Dried rhizome of *Tripterygium wilfordii* Hook. f. was extracted in refluxing 95% ethanol (the volume mass ratio of ethanol to dried rhizome of *tripterygium* wilfordii Hook. f. is 4-16:1) for 3-12 h. The extraction solution was concentrated under reduced pressure to obtain crude extract. The crude extract was adsorbed with neutral alumina and the ethanol was evaporated. Then it was extracted with chloroform and the solvent was evaporated under reduced pressure to obtain *tripterygium* glycosides.

According to another aspect of the disclosure, the disclosure provides a preparation method of the low toxic *tripterygium* neoglycosides, characterized in that, comprising the following steps:

a) Dried rhizome of *Tripterygium wilfordii* Hook. f. was extracted in refluxing 95% ethanol (the volume mass ratio of ethanol to dried rhizome of *Tripterygium wilfordii* Hook. f. is 4-16:1) for 3-12 h. The extraction solution was concentrated under reduced pressure to obtain crude extract. The crude extract was adsorbed with neutral alumina and the ethanol was evaporated. Then it was extracted with chloroform and the solvent was evaporated under reduced pressure to obtain *tripterygium* glycosides;

b) In a buffer solution prepared by sodium dihydrogen phosphate and phosphoric acid with a pH of 3.0-5.0, *tripterygium* glycosides (save some sample for triptolide detection) are heated to reflux for hydrolysis reaction for 18-96 h (preferably 30 h) in an oil bath at 90-120° C.;

After the reaction is completed, the solvent is removed under reduced pressure (or by extraction). The residue was redissolved in anhydrous ethanol, centrifuge. Insoluble substances were removed. Quantitively transfer some filtrate to volumetric flask and anhydrous ethanol was added to volume, HPLC analysis to calculate the amount of triptolide in the sample and the reduction amount of triptolide in the hydrolyzed product.

c) Triptriolide-anhydrous ethanol solution was added to the reaction product in step (b), mixed and, the solvent was removed to obtain low toxic *tripterygium* neoglycosides; the amount of triptriolide added was 0-20 times of the reduction amount of the triptolide in molar ratio.

Anhydrous ethanol in steps (1) and (2) can also be replaced by other nontoxic organic solvents, such as isopropanol.

According to another aspect of the disclosure, the disclosure provides the application of the low toxic *tripterygium* glycosides in the pharmaceutical preparation and treatment of nephrotic syndrome, primary glomerular nephropathy, purpuric and lupus nephritis, rheumatoid arthritis, lupus erythematosus, subacute and chronic severe hepatitis, chronic active hepatitis; allergic skin vasculitis, dermatitis, eczema, psoriatic arthritis and ankylosing spondylitis.

Both triptolide and triptriolide are diterpenoid components of *tripterygium* glycosides Hook. f. The chemical structures of the two are similar and can be mutually converted under certain conditions. In the disclosure, triptolide is converted into triptriolide on the basis of reflux reaction in a buffer solution prepared by sodium dihydrogen phosphate and phosphoric acid at a pH of 3.0-5.0, and *tripterygium* glycosides are integrally subjected to chemical processing under the same conditions, so that the triptolide content in the glycoside is reduced, and the toxicity of the preparation is reduced. However, while reducing toxicity, the efficacy of the preparation is correspondingly weakened. Therefore, the disclosure supplements a certain amount of triptriolide of low toxicity but effective (larger therapeutic index) to increase the effect of the preparation. According to the disclosure, for the first time, the content of triptolide is reduced, and the content of triptriolide is correspondingly increased, so that equivalent anti-inflammatory activity is ensured, and immunosuppression toxicity is reduced, thus providing a material basis for the application of triptolide in other pharmaceutical preparations and the treatment of clinical diseases.

The low toxic *tripterygium* neoglycosides have the following advantages:

1. Compared with the commercial *tripterygium* glycosides preparation, the toxicity of *tripterygium* neoglycosides is greatly reduced ($p<0.05$);

2. *Tripterygium* neoglycosides can effectively relieve renal pathological injury and low urinary protein of nephrotic syndrome, attenuate inflammation level, and show obvious therapeutic effect on nephrotic syndrome and sustained curative effect.

3. Because immune-related diseases have similar pathological mechanism, the *tripterygium* neoglycosides provided by the disclosure can also play a therapeutic role on other immune-related diseases, especially inflammation-mediated immune-related diseases, and have an attenuation effect.

BRIEF DESCRIPTION OF THE DRAWINGS

FIG. 15 shows a pathological optical microscope results.

DETAILED DESCRIPTION

The disclosure will be described in further detail below by ways of examples.

The common reagents used in the following preparation examples are all commercially available reagents, and the instruments used are:

Ultra-high performance liquid chromatography (Waters Acquity, Waters of the United States), 1/10,000 balance (AL104-IC, METTLER TOLEDO of Switzerland), 1/100,000 balance (AB135-S, METTLER TOLEDO of Switzerland), PH meter (PHS-3C, Shanghai Precision Instrument Co., Ltd.), magnetic stirrer (HS7, IKA of Germany), rotating thin film evaporator (RV 10 basic V, IKA of Germany), micro centrifuge (Microfuge16, BACKMAN of the United States), full wavelength enzyme labeler (1510, Thermo Fisher Scientific (China) Co., Ltd.), thermo scientific pipette gun, 1-10 µL, 10-100 µL, 100-1000 µL (Thermo Fisher Scientific. Inc.), protein vertical electrophoresis membrane transfer system (Bio-Rad), automatic immunoassay analyzer (Abbott), Leica Slicer (Leica).

1. Preparation of *Tripterygium* Neoglycoside 1,500 g of dried rhizome of *Tripterygium wilfordii* Hook. f., 12 L of 95% ethanol is refluxed for 10 hours. The extract is concentrated under reduced pressure to obtain crude extract. The crude extract is adsorbed with neutral alumina, the ethanol is evaporated. Then it is extracted with 5 L of chloroform, and the extraction concentrated under reduced pressure to obtain *tripterygium* glycosides.

The prepared *tripterygium* glycosides are sampled to detect the content of triptolide, and compared with the *tripterygium* glycosides sold on the market through their fingerprints and characteristic components. By comparison, the obtained *tripterygium* glycosides are equivalent to the fingerprints of the mainstream products on the market: *tripterygium* glycosides preparation produced by Shanghai Fudan Fuhua Pharmaceutical Co., Ltd., Hunan Qianjin Xieli Pharmaceutical Co., Ltd., China Resources Sanjiu Pharmaceutical Co., Ltd., and *Tripterygium wilfordii* Hook. f. tablets of Hunan Xieli Pharmaceutical Co., Ltd.

Dissolving sodium dihydrogen phosphate in water, adding 1 vol % phosphoric acid solution to adjust pH to 4.0 at room temperature to obtain sodium dihydrogen phosphate/phosphoric acid buffer solution with pH of 4.0.

Figure 16:
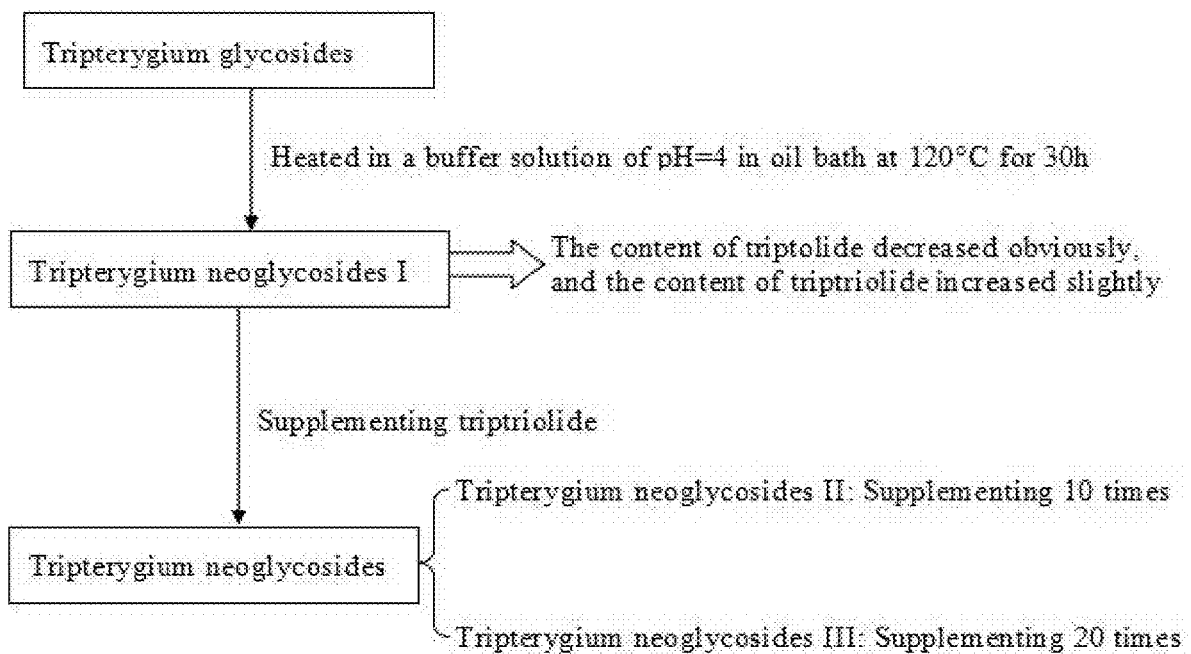
FIG. 16 shows the process of obtaining *tripterygium* glycosides I, II and III.

In a sodium dihydrogen phosphate/phosphoric acid buffer solution with a pH of 4.0, the prepared *tripterygium* neoglycosides are heated to reflux in oil bath at 90-120° C. for hydrolysis reaction for 30 h. After the solvent is removed under reduced pressure, anhydrous ethanol is added for redissolution. The mixture is centrifuged and insoluble substances are removed, and anhydrous ethanol is added to volume 1 L. 10 mL is analyzed and the reduction amount of triptolide is calculated. Then 300 mL is sampled and the solvent is directly evaporated to obtain *tripterygium* neoglycosides I; sampling another 300 mol, adding triptriolide-ethanol solution with 10 times (molar ratio) reduced amount of triptolide, evaporating the solvent to obtain *tripterygium* neoglycosides II; sampling another 300 mol, adding triptriolide-ethanol solution with 20 times (molar ratio) reduced amount of triptolide, and the solvent is evaporated to obtain *tripterygium* neoglycosides III, which is stored in a refrigerator at −20° C. *Tripterygium* neoglycosides I, II and III are obtained by the above methods. The specific operation flow is shown in FIG. 16.

2. Determination of Triptolide and Triptriolide in *Tripterygium* Neoglycosides I, II and III.

Figure 1:
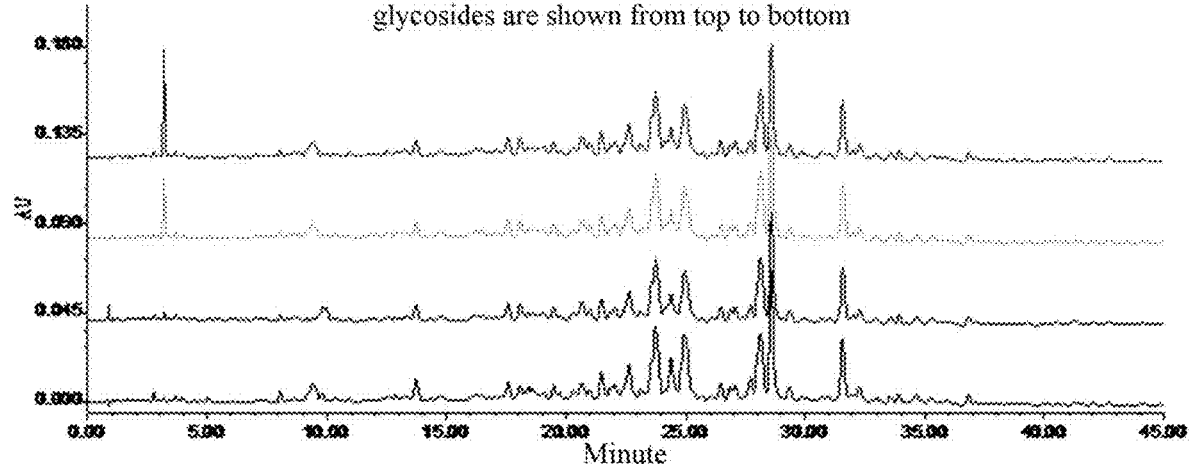
FIG. 1 shows chromatograms of *tripterygium* glycosides and *tripterygium* neoglycosides I, II and III.
Figure 2:
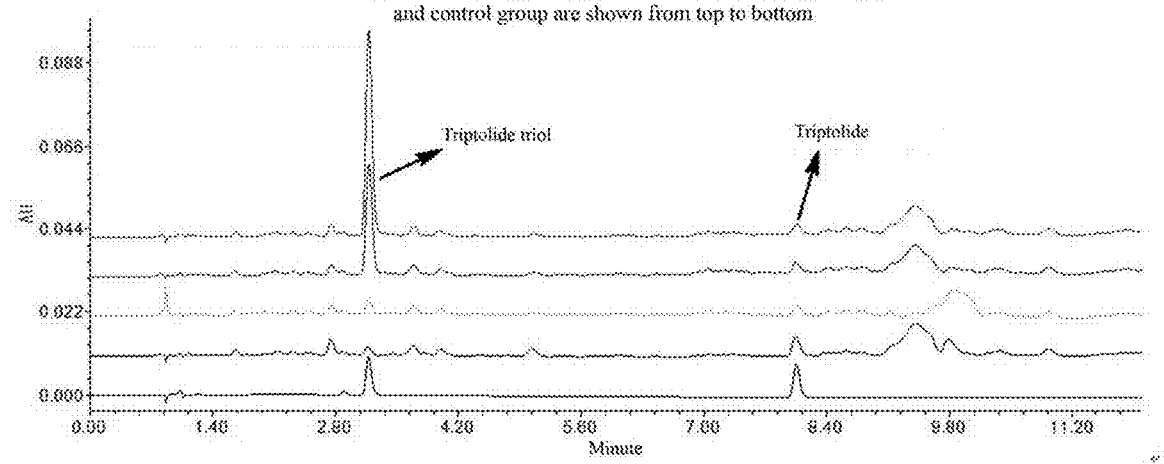
FIG. 2 shows chromatograms of FIG. 1 after adding reference standards.

HPLC detection conditions: column: waters BEH Shielded RP18 (2.1×100 mm, 1.7 μm); mobile phase: acetonitrile-water system; gradient elution, elution procedures are shown in table 1; flow rate: 0.3 mL/min; detection wavelength: 220 nm; column temperature: 35° C.; injection volume: 3 μL; the results are shown in FIGS. 1 and 2.

TABLE 1

| | Time (min) | | | | |
|---|---|---|---|---|---|
| | 0 | 5 | 6 | 12 | 20 |
| Acetonitrile (%) | 15 | 20 | 25 | 27 | 35 |
| Water (%) | 85 | 80 | 75 | 73 | 65 |

In FIG. 2, the reference substance is a mixture of triptolide and triptriolide. As can be seen from FIGS. 1 and 2, triptolide in *tripterygium* neoglycosides I, II and III is less than that in *tripterygium* glycosides. The content of triptriolide in *tripterygium* neoglycosides I and *tripterygium* glycosides is extremely low, while the content of triptriolide in *tripterygium* neoglycosides II and *tripterygium* neoglycosides III is high.

Using triptolide and triptriolide as standard, the contents of triptolide and triptriolide in *tripterygium* glycosides and *tripterygium* neoglycosides I, II and III can be obtained by HPLC quantitative analysis, as shown in table 2.

TABLE 2

| Contents of symbolic components in tripterygium glycosides and tripterygium neoglycosides (n = 3) | | |
|---|---|---|
| | Triptolide (μg/g) | Triptriolide (μg/g) |
| Tripterygium glycoside | 442.50 ± 5.54 | 204.44 ± 3.21 |
| Tripterygium neoglycosides I | 228.71 ± 2.14 | 298.88 ± 1.41 |
| Tripterygium neoglycosides II | 227.47 ± 1.98 | 2450.01 ± 11.56 |
| Tripterygium neoglycosides III | 226.33 ± 2.24 | 4568.49 ± 28.90 |

3. Bioassay Experiment on Cells 3.1 Cell Culture of HK-2, HL-7702, GC1, GC2, TM4 and Toxicity Test HK-2, HL-7702, GC1, GC2, TM4 were all purchased from ATCC; HK-2: 37° C. DMEM/F12+10% FBS+1% Pen Strep; HL-7702, GC1, GC2, TM4 are all DMEM+10% FBS+1% Pen Strep at 37° C.; finally, they were all placed in an incubator containing 5% $CO_2$ and cultured until the 80% of cells were adhered to the wall. Cells in logarithmic growth phase are digested with 0.25% trypsin, then seeded in a 96-well plate with appropriate cell density. After adhering to the plate in a monolayer, the cells were cultured in a synchronized medium and synchronized for 12 hours. After entering the quiescent phase, the cells were treated with glycosides: *tripterygium* glycosides (LGT 0, 1, 5, 10, 20, 30, 50, 100 μg/mol), *tripterygium* neoglycosides II (LGT-2, 0, 1, 5, 10, 20, 30, 50, 100 μg/mol), *tripterygium* neoglycosides III (LGT-4, 0, 5, 10, 20, 30, 50, 75, 100 μg/mol), LGT-5 (0, 0.1, 2.5, 5, 10, 15, 25, 50 μg/mol), triptolide (0, 1, 5, 15, 25, 40, 80, 150 ng/mol), triptriolide (0, 50, 100, 200, 250, 300, 400, 500 μg/mol), mix (triptolide:triptriolide=1:10, 0, 22, 88, 110, 330, 660, 990, 2200 ng/mL). 220 μL of chemicals is added each time and culture for 24 hours. MTT assay test was performed to detect cell activity and $IC_{50}$ value was calculated after 24 hours of administration and the results are shown in FIG. 3.

Figure 3:
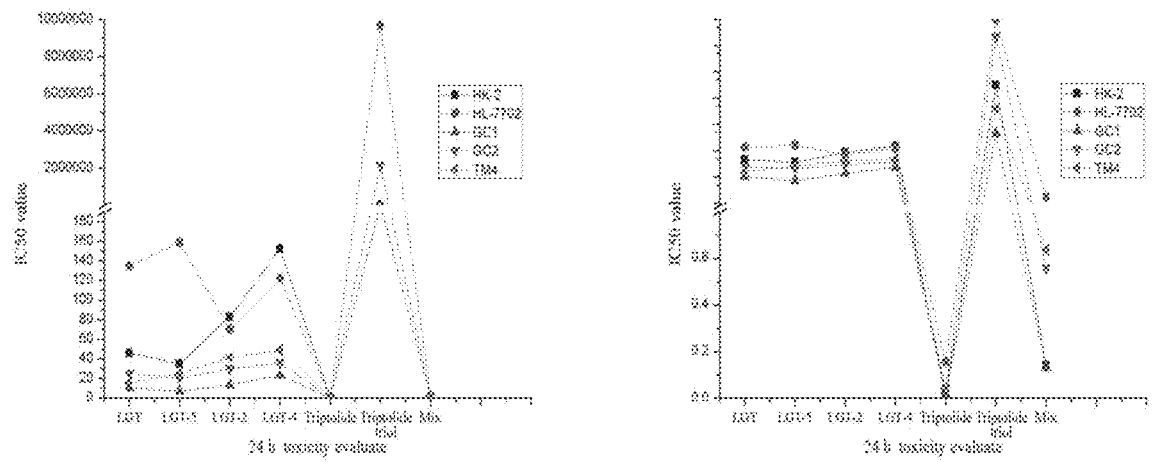
FIG. 3 is a graph showing toxicity results of *tripterygium* neoglycosides in various cell lines.

In FIG. 3, the left side is an enlarged view of $IC_{50}$ value in section 0-200, and the right side is an enlarged view of $IC_{50}$ value in section 0-1 (due to large difference in activity, the longitudinal axis is truncated and in two magnifications). As can be seen from FIG. 3, the toxicity of *tripterygium* neoglycosides group to each cell line is significantly reduced, and the toxicity of each preparation is about 1000 times lower than that of triptolide on average. When the ratio of triptriolide to triptolide is 10:1 (close to the ratio of *tripterygium* neoglycosides II), the toxicity of the mixed triptriolide and triptolide is reduced by about 100 times which considered to be significant.

3.2 Detection of Immunosuppressive Activity:

The rats were sacrificed by neck amputation and soaked in 75% ethanol. The spleens of the rats were taken out in an ultra-clean bench, washed in DPBS for 3 times, fully moistened, 200 mesh gauze was placed on a dish (35 mm diameter), it is evenly ground in one direction by a piston of a 10 mL syringe, the spleen was moistened with DPBS while grinding. The collected lymphocyte suspension was centrifuged at 1500 rpm for 3 min, and 7 mL of erythrocyte lysate was added to each spleen suspension. After acting at room temperature for 30 min, the cells were centrifuged at 1500 rpm for 3 min. After discarding supernatant, the cells were washed with DPBS for 3 times to remove excess serum, added with 4 mol of 70% Percoll to the bottom layer of 15 mL centrifuge tube and 4 mol of 40% Percoll to the upper layer of 15 mL centrifuge tube, then centrifuged 800 g at room temperature for 20 min on a horizontal centrifuge. After sucking cells between 40% Percoll and 70% Percoll, the cells were washed with 4 mL DPBS for 3 times; inoculated into 96-well culture plates, and treated with 200 μL of chemicals: blank control group (only adding culture medium), triptriolide with different concentrations (50, 100, 150, 200 μg/mL), T lymphocyte specific increment inducer Con A (10 μg/mL, corresponding to normal inhibition group) and B lymphocyte specific increment inducer LPS (10 μg/mL, corresponding to normal inhibition group), each; the cells were cultured in a 5% $CO_2$ incubator at 37° C. and MTT method was used to detect the cell activity and inhibition rate 24 hours later. The results are shown in FIG. 4.

The pretreatment of lymphocytes in the specific inhibition experiment is the same as above. After lymphocytes inoculated into 96-well culture plates, drug was added. 200 μL of drug was added each to blank control group (culture medium only), T lymphocyte specific increment inducer Con A model group (5 μg/mL, corresponding model group) and B lymphocyte specific increment inducer LPS model group (5 μg/mL, corresponding model group). Con A administration group was firstly added multiple doses of T lymphocyte specific increment inducer Con A 100 μL (10 μg/mol, corresponding model group) separately, and then added 100 μL of triptriolide (100, 200, 300, 400 μg/mL) with different concentrations separately. In LPS administration group, multiple doses of B lymphocyte specific increment inducer LPS 100 μL (10 μg/mol, corresponding model group) were added respectively, and 100 μL of triptriolide (100, 200, 300, 400 μg/mL) with different concentrations were added respectively. Each group was cultured in an incubator at 37° C. and 5% $CO_2$, and the cell activity and inhibition rate were detected by MTT method 24 hours later. The results are shown in FIGS. 4 and 5.

Figure 4:
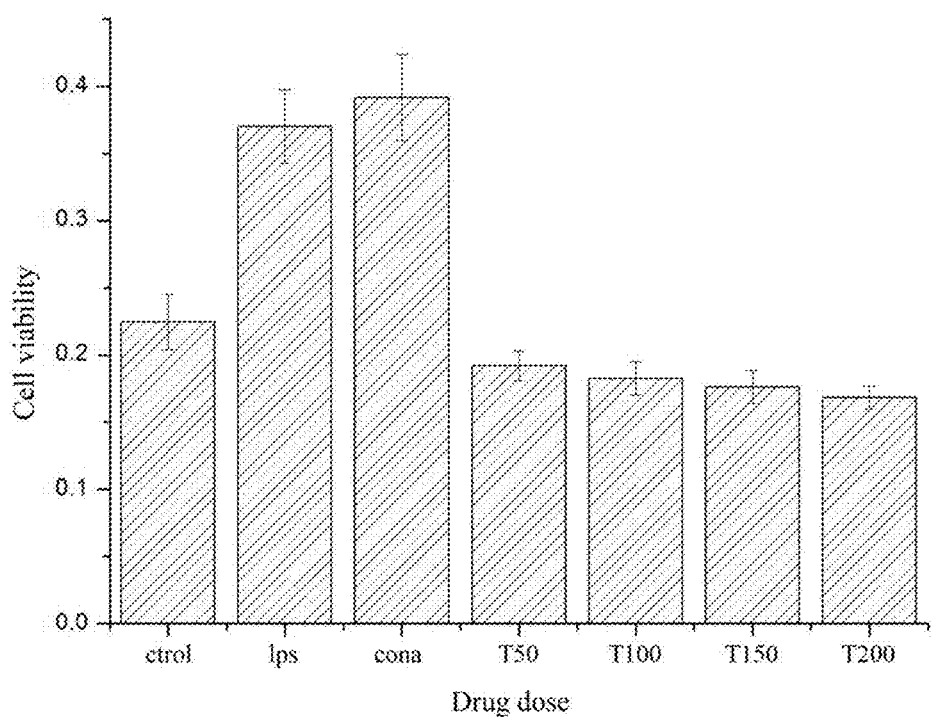
FIG. 4 is a graph showing the result of triptriolide inhibiting normal TB lymphocyte increment.

It can be seen from FIG. 4 that triptriolide has the effect of inhibiting increment of normal T and B lymphocytes in vitro, and the inhibitory effect is dose-dependent, and the cell activity of each administration group is significantly lower than that of the control group and model group $p<0.05$; 50 μg/mol of triptriolide and 200 μg/mol of triptriolide have significant difference in inhibition of cell activity ($p<0.05$).

Figure 5:
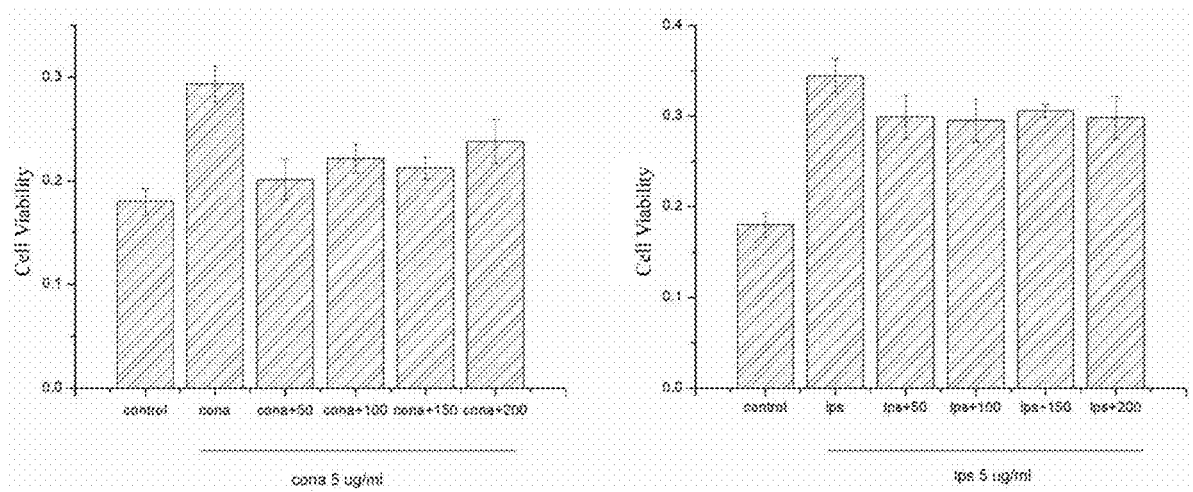
FIG. 5 is a graph showing the result of triptriolide inhibiting induced T/B lymphocyte increment.

It can be seen from FIG. 5 that after T cell specific inducer Con A and B cell specific inducer LPS are respectively added, and then treated with triptriolide of different concentrations, the cell activity of the administration groups are higher than that of the blank control group, but lower than that of the model group. Therefore, it can be seen that triptriolide does have lower immunosuppressive effect, and the immunosuppressive effect on T lymphocytes is significantly higher than that on B lymphocytes with $p<0.05$. The immunosuppressive effect on single cell did not show dose-dependence.

3.3 Anti-Inflammatory Activity

Raw264.7 37° C., 5% $CO_2$ RPMI-1640+10% FBS+1% Pen Strep. Finally, the cell was cultured in an incubator until 80% of the cells adhere to the wall. The cells in logarithmic growth phase were taken and adjusted to the appropriate cell density in a 96-well plate after digestion with 0.25% trypsin. After adhering to the wall in monolayer, the cell was cultured in a synchronized medium for 12 hours. After entering the quiescent period, except for the blank control group, 1 mL of LPS (1 μg/mL) was used as a modeling agent in other groups to induce the cell inflammation model in the cell in each group. Meanwhile, drug treatment is carried out: 1 mL of culture medium was added to the model group, 1 mL of liquid drug with corresponding concentration was added to the drug administration group (triptolide 50, 100, 150, 200 μg/mL dose group), and 2 ml of culture medium was directly added to the blank control group. Western blot, qPCR, ELISA and other methods were used to detect the expression levels of inflammation-related proteins, genes, cytokines, the expressions of NF-κB transcription-related factors, and the expressions of IL-6, IL-10, TNF-α and other inflammatory cytokines in different treatment groups.

Figure 6:
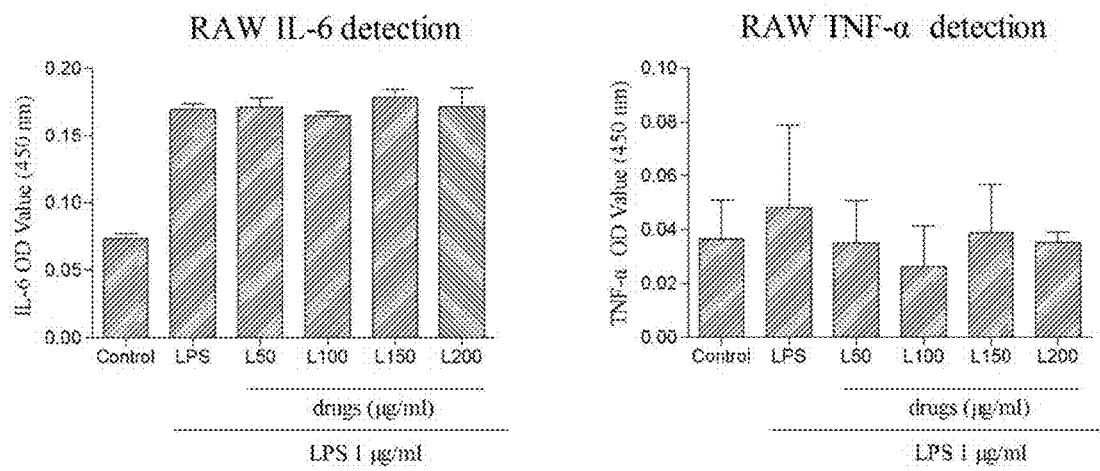
FIG. 6 is a graph showing the results of triptriolide inhibiting Raw264.7 cell inflammatory factors.

As shown in FIG. 6, studies in vivo and in vitro show that TNF-α is mainly secreted by mesangial cells, epithelial cells or monocyte macrophages on inflamed glomeruli, which not only stimulates mesangial cells to divide and proliferate, but also stimulates mesangial cells to secrete a variety of inflammatory cytokines, aggravating the increment of mesangial cells. Cytokine TNF-α has an important inflammatory effect. The results of this study show that triptriolide can improve cytokine secretion in LPS-induced inflammatory injury model of rat macrophages.

Figure 7:
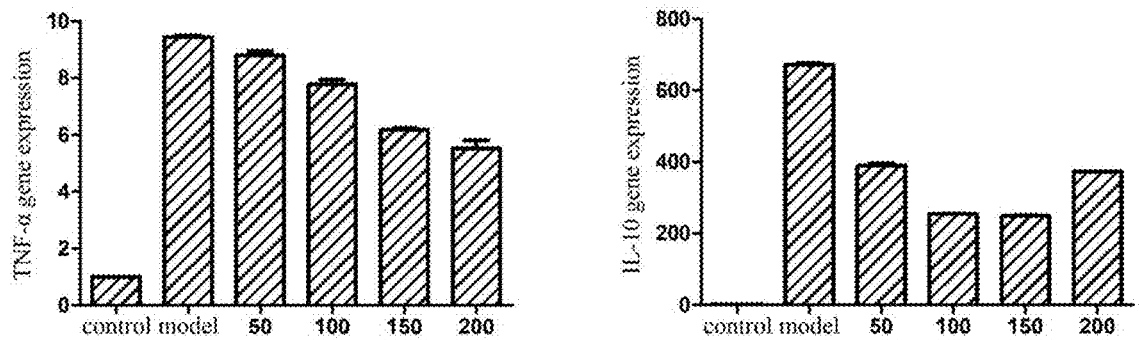
FIG. 7 is a graph showing the results of triptriolide inhibiting Raw264.7 cell inflammatory genes.
Figure 8:
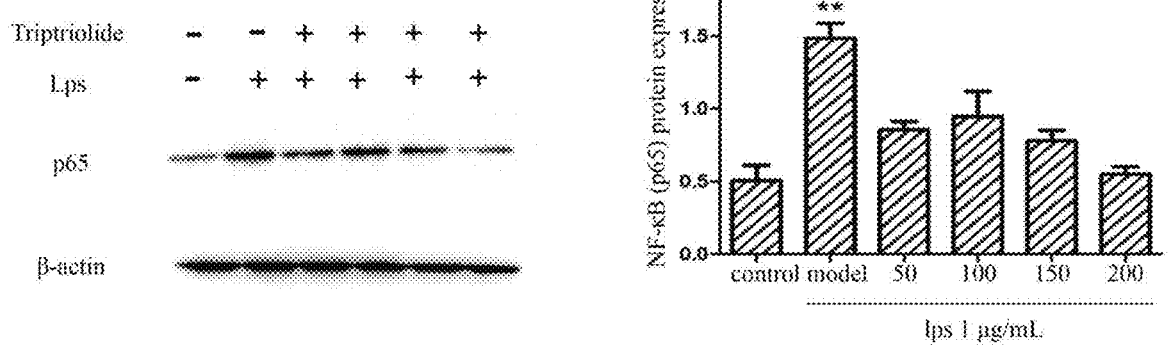
FIG. 8 is a graph showing the expression results of triptriolide r inhibiting Raw264.7 cells NF-κB protein expression level.

As shown in FIGS. 7 and 8, NF-κB P65 plays an important role in humoral and cellular immunity by regulating the expression of TNF-α, IL-6, IL-10 and other inflammatory cytokine genes, thus affecting the body's inflammatory response and regulating the increment, growth and differentiation of T and B cells. It can be seen from the figures that triptriolide can effectively reduce the effects of inflammatory factors TNF-α and IL-10. The expression of IL-10 can be increased at high concentration. This suggests that the drug can effectively reduce the transcription of inflammatory factors and has certain immunoregulatory activity.

4 Experiment of Triptriolide on Protecting Podocyte from Apoptosis

Rat immortalized podocyte cell line MPCS is presented by nephrology department of Guangdong provincial hospital of Traditional Chinese Medicine. The treatment methods of MCP5 are presented as follows: Western blot, IFC, qPCR, ELISA and other methods are used to detect the expression levels of inflammation-related proteins, genes and cytokines in different treatment groups. The podocyte cell is temperature sensitive cell, increases at 33° C. RPMI-1640+10% FBS+1% Pen Strep+10 U/mL γ-IFN, and differentiates at 37° C. RPMI-1640+10% FBS+1% Pen Strep medium for 10-14 days. The MCP5 treatment method is presented as follows: except for the blank control group, 1 mL of ADM (0.8 μg/mL) was used as a modeling agent in other groups to induce cell apoptosis model, and the drug was added at the same time: 1 mL of culture medium was added to the model group, 1 mL of drug solution with corresponding concentration was added to the administration group (triptolide 50, 100, 150, 200 μg/mol, dose group), and 2 mL of culture medium was directly added to the blank control group; Western blot, IFC, qPCR, ELISA and other methods were used to detect the expression levels of inflammation-related proteins, genes and cytokines in different treatment groups. The expression of podocaine membrane protein podocine and apoptosis-related gene Bax were detected by flow cytometry using FITC-labeled Annexin V and Propidium iodide (PI) to differentiate early apoptotic cells from late apoptotic cells and dead cells. The results are shown in FIG. 9, FIG. 10 and FIG. 11.

Figure 9:
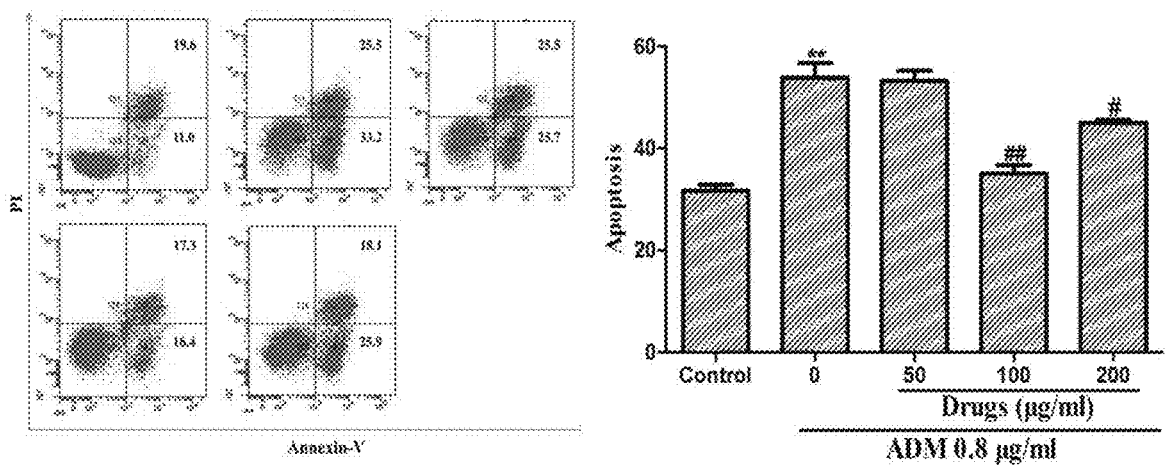
FIG. 9 is a graph showing the results of triptriolide inhibiting podocyte apoptosis.
Figure 10:
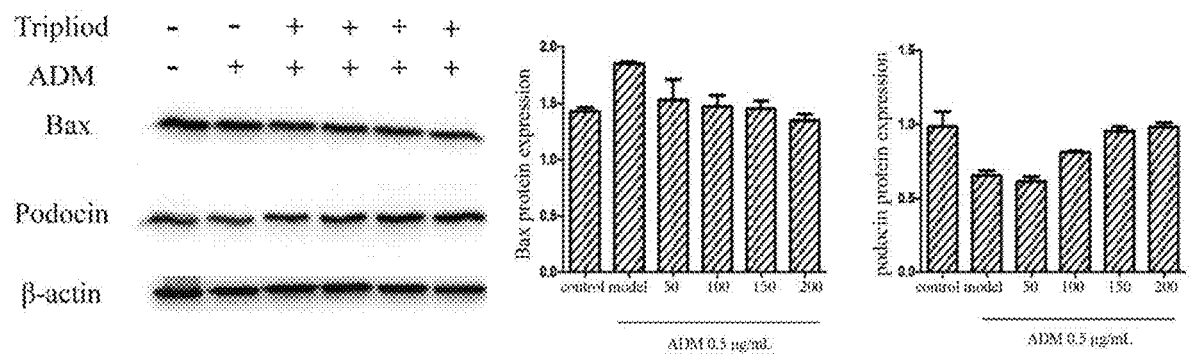
FIG. 10 is a graph showing the expression results of podocyte marking protein podocin and apoptotic protein Bax.
Figure 11:
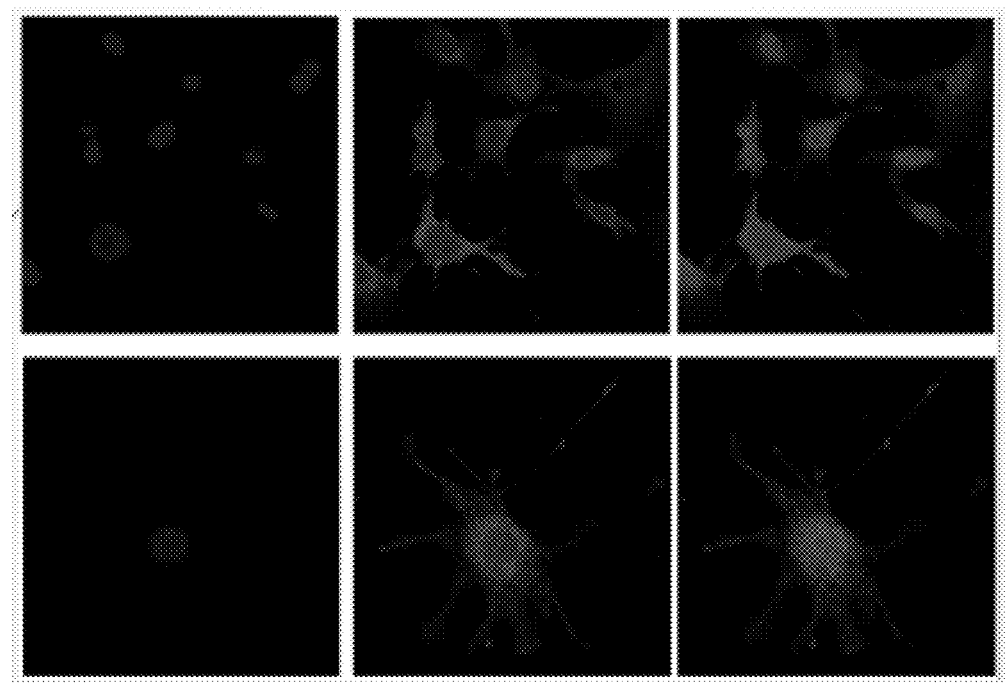
FIG. 11 is a laser confocal diagram showing the result of podocyte marking protein expression.

As shown in FIGS. 9 to 11, podocytes undergo apoptosis, autophagy and necrosis after injury, resulting in a decrease in their number and eventually urinary protein, affecting renal function. Based on the results, we know that fully differentiated podocytes turned into apoptosis cell model by using 0.8 μg/mL ADM. After treatment with triptriolide, the apoptosis of cells is attenuated, which suggests that triptriolide has the effect of protecting podocyte from injury and can be used for clinical podocyte disease treatment. The experimental results show that triptriolide can protect podocyte from apoptosis, but it has an upward trend at high concentration.

5 In Vivo Experiments 5.1 Establishment of Nephrotic Syndrome Model in Rat Induced by Adriamycin (ADR)

100 healthy male SD rats were fed for 7 days, and then 8 rats were randomly selected as blank control group. The remaining rats were injected adriamycin at a dose of 5.0 mg/kg into caudal vein to induce adriamycin nephrotic syndrome animal model without anesthesia.

Grouping: After 3 weeks of adriamycin injection, 24-hour urinary protein excretion was measured in 100 rats. Compared with the blank group (injected with the same amount of normal saline), the rats that successfully modeled were determined. Rats with 24 hours urinary protein excretion of 70-180 mg are randomly and equally divided into model group, *tripterygium* glycosides group, *tripterygium* neoglycosides I group, *tripterygium* neoglycosides II group and *tripterygium* neoglycosides III group according to urinary protein excretion. The content ratio results are the same as those in Table 2.

TABLE 2

Contents of tripterygium glycosides and
tripterygium neoglycosides (n = 3)

| | Triptolide (µg/g) | Triptriolide (µg/g) |
|---|---|---|
| Tripterygium glycoside | 442.50 ± 5.54 | 204.44 ± 3.21 |
| Tripterygium neoglycosides I | 228.71 ± 2.14 | 298.88 ± 1.41 |
| Tripterygium neoglycosides II | 227.47 ± 1.98 | 2450.01 ± 11.56 |
| Tripterygium neoglycosides III | 226.33 ± 2.24 | 4568.49 ± 28.90 |

5.2 Selection of Dosage

Preparation of the drug: 0.4 g of *tripterygium* glycosides are taken, 5 mL of anhydrous ethanol was added to dissolve the drug, the anhydrous ethanol solution was slowly dripped into the sodium carboxymethyl cellulose solution and volume to 423 mL. The mixture was shaken clockwise while being added, and then the mixture is sonicated. The preparation method of *tripterygium* neoglycosides I, II and III was the same as *tripterygium* glycosides, and the final concentration was 0.95 g/L.

From the next day after successful modeling, each group was given gastric lavage daily, and the blank group and the model group were given normal saline; *tripterygium* glycosides group was given *tripterygium* glycosides (0.95 g/L); *tripterygium* neoglycosides I, II, III (0.95 g/L) group were given *tripterygium* neoglycosides I, II and III, respectively for 8 weeks. The intragastric dose of each rat was 1 mL/(100 g rats)

5.3 Detection of Observation Indexes

Animal conditions: rats in each group were weighed twice a week, and their mental state, body hair, edema and activity were observed.

Figure 12:
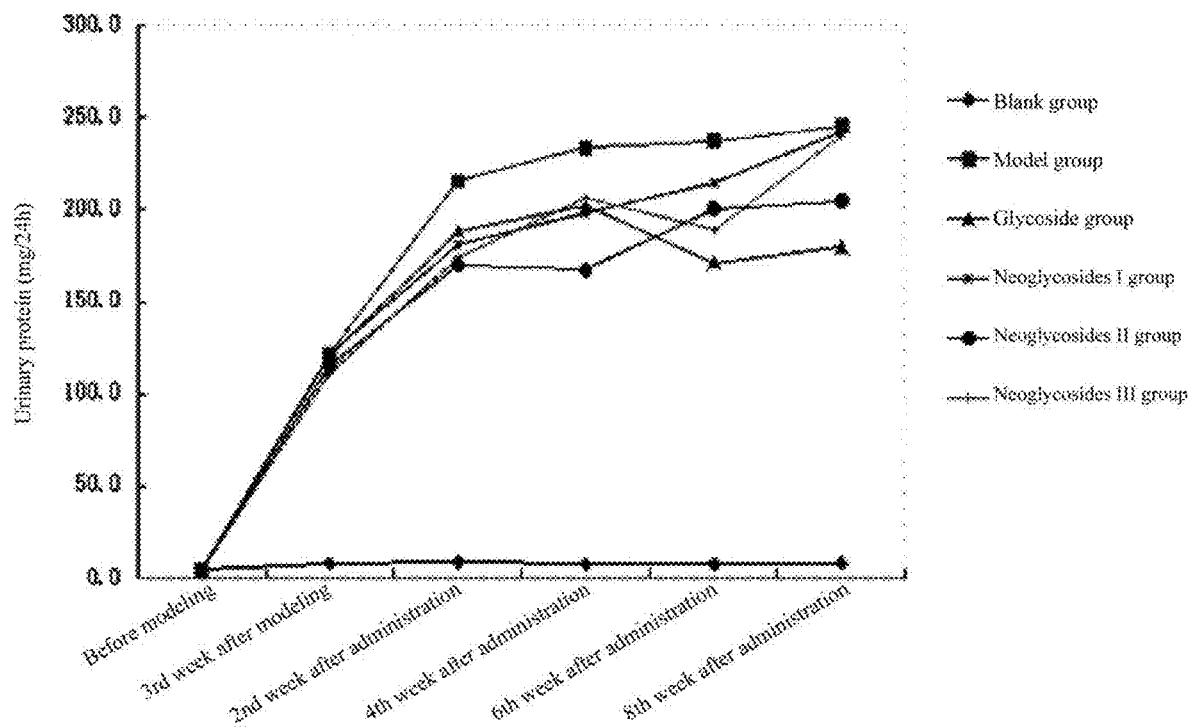
FIG. 12 is a trend graph showing the urinary protein levels of NS rats in each experimental group.

Determination of urinary protein content: rats in each group were separately placed in metabolic cages at the 3rd week after modeling and the 2nd, 4th, 6th and 8th week after administration. 24-hour urine was collected and the urine volume was recorded. Urinary protein concentration was determined by Coomassie Brilliant Blue method and 24-hour urinary protein excretion was calculated. The results are shown in table 3, table 4 and FIG. 12.

TABLE 3

24-hour urinary protein excretion of rats in each group
before administration (mg, n = 8, $\bar{x}$ ± SD)

| | N | Before molding | 3rd week after modeling |
|---|---|---|---|
| Blank group | 8 | 5.2 ± 1.4 | 7.9 ± 1.4 |
| Model group | 8 | 5.0 ± 1.0 | 121.6 ± 40.7** |
| Glycoside group | 8 | 3.9 ± 0.6 | 120.2 ± 48.1** |
| Neoglycosides I group | 8 | 4.8 ± 1.0 | 120.8 ± 35.8** |
| Neoglycosides II group | 8 | 4.2 ± 1.0 | 115.1 ± 35.7** |
| Neoglycosides III group | 8 | 4.2 ± 0.3 | 111.3 ± 32.3* |

Compared with the blank group, *p < 0.05, **p < 0.01

TABLE 4

24-hour urinary protein excretion (mg, n = 8, $\bar{x}$ ± SD) of rats in each group after administration

| | 2nd week after administration | 4th week after administration | 6th week after administration | 8th week after administration |
|---|---|---|---|---|
| Blank group | 8.8 ± 1.7 | 7.8 ± 1.4 | 7.9 ± 1.1 | 8.5 ± 1.5 |
| Model group | 215.8 ± 38.2* | 233.7 ± 45.6** | 237.5 ± 56.4* | 245.8 ± 64.1* |
| Glycoside group | 188.4 ± 77.5# | 202.2 ± 84.1# | 171.4 ± 74.6# | 179.8 ± 45.1# |
| Neoglycosides I group | 181.0 ± 53.7 | 198.5 ± 72.9 | 214.9 ± 94.6 | 242.3 ± 95.2 |
| Neoglycosides II group | 169.9 ± 18.7## | 167.7 ± 48.6## | 201.0 ± 51.1## | 205.0 ± 52.0## |
| Neoglycosides III group | 174.5 ± 38.4 | 206.6 ± 59.8 | 188.9 ± 66.5 | 240.1 ± 83.5 |

Compared with blank group, *p < 0.05, **p < 0.01;
Compared with model group, #p < 0.05, ##p < 0.01

The results (Table 3, Table 4 and FIG. 12) showed that the rats in the blank group have good mental state, shiny body hair, normal activities and diet, and normal urine volume during the whole experimental process. Two weeks after modeling, the water drinking amount and urine volume of the model group were reduced, and some rats appeared rot tail. After administration, the rats in the model group were restless all the time, with messy body hair, reduced urine volume and emaciation. Compared with the model group, the above performance of each group was improved after administration.

The data at all time points was analyzed by SPSS 20.0 statistical software, and was conformed to fit the normal distribution. Before modeling, there is no significant difference in urinary protein excretion among the groups. At the 3rd week of modeling, urinary protein excretion of rats in each modeling group is significantly different from that in the blank group (p<0.01), suggesting that modeling is successful. In the course of treatment, urinary protein excretion of rats in each treatment group decreased to different degrees. After the administration, the urinary protein excretion in *tripterygium* glycosides group and neoglycosides II group decreased significantly (p<0.05) compared with the model group. However, there is no significant difference in urinary protein excretion between *tripterygium* glycosides group and neoglycosides II group.

Figure 13:
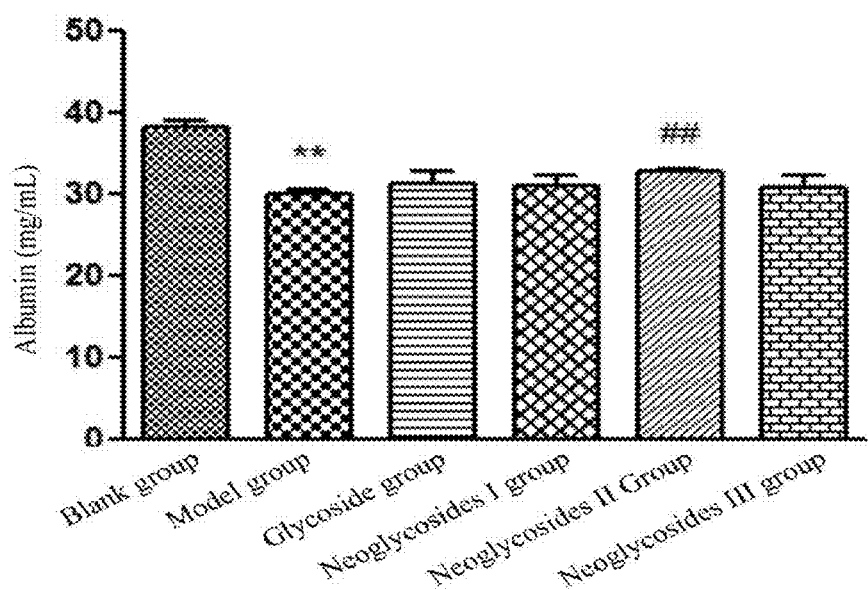
FIG. 13 is a schematic graph showing the urinary protein levels of NS rats in each experimental group.
Figure 14:
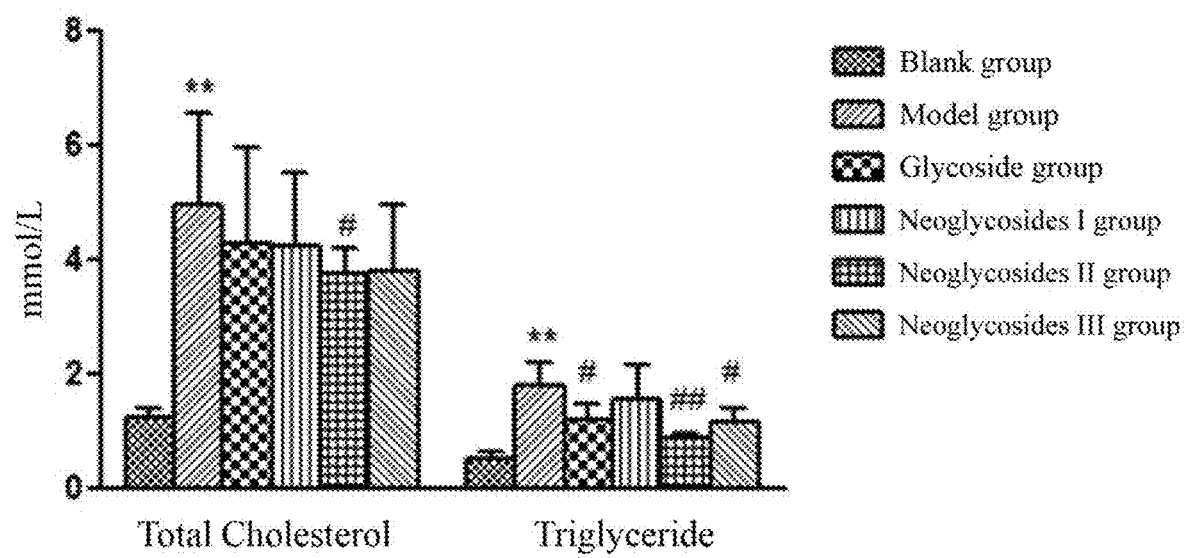
FIG. 14 is a schematic graph showing the effects of each experimental group on total cholesterol and triglyceride in NS rats.

Detection of blood biochemical indexes: at the end of the 8th week of the experiment, rat serum was taken by abdominal aorta blood sampling, and blood biochemical indexes such as total protein, albumin, urea nitrogen, creatinine, total cholesterol, triglyceride in the serum were determined by a fully automatic biochemical analyzer. The results are shown in table 5, FIG. 13 and FIG. 14.

TABLE 5

Results of Blood Biochemical Indexes of Rats in Each Group (n = 8, x̄ ± SD)

| | Total protein | Albumin | Urea nitrogen | Creatinine | Total cholesterol | Triglyceride |
|---|---|---|---|---|---|---|
| Blank group | 58.0 ± 2.3 | 38.4 ± 1.6 | 6.1 ± 0.7 | 32.5 ± 3.4 | 1.25 ± 0.17 | 0.52 ± 0.13 |
| Model group | 55.8 ± 1.1 | 30.0 ± 1.4** | 7.4 ± 1.3 | 31.4 ± 1.7 | 4.97 ± 1.60* | 1.82 ± 0.39* |
| Glycoside group | 55.9 ± 2.2 | 31.3 ± 4.2 | 6.6 ± 1.4 | 30.3 ± 3.8 | 4.28 ± 1.68 | 1.21 ± 0.28# |
| Neoglycosides I group | 54.7 ± 2.3 | 31.0 ± 3.4 | 6.1 ± 0.7 | 30.0 ± 3.9 | 4.25 ± 1.26 | 1.58 ± 0.57 |
| Neoglycosides II group | 56.4 ± 2.2 | 32.9 ± 0.8## | 6.3 ± 0.9 | 29.5 ± 2.2 | 3.75 ± 0.47# | 0.88 ± 0.10# |
| Neoglycosides III group | 53.7 ± 3.7 | 30.9 ± 3.9 | 6.6 ± 1.5 | 30.5 ± 3.2 | 3.81 ± 1.14 | 1.16 ± 0.26# |

Compared with the blank group, $*p < 0.05$, $**p < 0.01$;
compared with model group, $\#p < 0.05$, $\#\#p < 0.01$ The experimental results were analyzed by SPSS 20.0 statistical software and the data of all groups was conformed to be normal distribution. The experimental results show that: 1) There is no significant difference in the total protein level of rats in each group. The albumin level in the model group is significantly lower than that in the blank group ($p<0.01$). The albumin content in the neoglycosides II group is significantly increased with significant difference ($p<0.01$) compared with the model group. 2) There is no significant difference in serum urea nitrogen and creatinine levels among the groups. 3) Total cholesterol level: the total cholesterol level in the model group is significantly higher than that in the blank group ($p<0.01$). Compared with the model group, the total cholesterol level in the neoglycosides II group is significantly reduced with significant difference ($p<0.05$). 4) Triglyceride level: compared with the blank group, the triglyceride level in the model group is significantly increased ($p<0.01$). Compared with the model group, the total cholesterol levels in the glycoside group, the neoglycosides II and III groups are significantly reduced ($p<0.05$ or $p<0.01$).

Histopathological examination: After taking blood from abdominal aorta, the kidneys of rats were extracted, fixed with 10% formalin solution, embedded in paraffin and sectioned, and stained with HE for pathological examination. The results are shown in FIG. 15. It can be seen from the results that there is no obvious abnormality in glomerulus, renal tubules and renal interstitium in the blank group under microscope. In the model group, mesangial cells and stroma proliferate, fibrosis in renal interstitial, granular degeneration can be seen in some renal tubular epithelial cells, and atrophy can be seen in some glomeruli. Renal pathology in each treatment group is improved compared with that in the model group.

To sum up, NS rats cause a large amount of albumin to leak into urine and form a large amount of urinary protein due to impaired glomerular barrier function. Therefore, for the treatment of NS diseases, an important indicator is to reduce urinary protein excretion in NS rats. However, when glomerular damage is severe and glomerulosclerosis occurs, urinary protein excretion may also be significantly reduced, resulting in false positive results. Therefore, in order to judge the curative effect of drugs on NS diseases, besides observing the excretion of urinary protein, comprehensive evaluation should be made in combination with the levels of serum creatinine, urea nitrogen and pathological examination results of kidney. The experimental results show that *tripterygium* neoglycosides II can significantly reduce 24-hour urinary protein excretion in NS rats, and creatinine and urea nitrogen levels are not abnormal, and no obvious pathological changes such as glomerulosclerosis are found in renal pathological sections of neoglycosides II group. Therefore, *tripterygium* neoglycosides II have significant therapeutic effect on NS rats. Pharmacodynamics results show that NS animal model can be successfully established by injecting 5 mg/kg adriamycin into tail vein of rats disposablely. It can be seen from the drug intervention that *tripterygium* glycosides and *tripterygium* neoglycosides II have significant therapeutic effects on NS rats. The drug effects of the two are similar, but *tripterygium* neoglycosides II take effect faster. The *tripterygium* neoglycosides II obtained in this experiment achieve the purpose of persistence in the study of a new technology of toxicity reduction and persistence. Therefore, the neoglycosides from *Tripterygium wilfordii* Hook. f. of the disclosure provide a basis for the application of drugs for preparing and treating nephrotic syndrome, primary glomerular nephropathy, purpuric and lupus nephritis, rheumatoid arthritis, lupus erythematosus, subacute and chronic severe hepatitis and chronic active hepatitis; allergic skin vasculitis, dermatitis, eczema, psoriatic arthritis and ankylosing spondylitis, which proved to be feasible.

What has been described above is only some embodiments of the disclosure. For those of ordinary skilled in the art, several modifications and improvements can be made without departing from the inventive concept of the disclosure, which are all within the scope of protection of the disclosure.

What is claimed is:

1. A method for preparing low toxic *tripterygium* glycosides, characterized by comprising the following steps:
   a) dried rhizome of *Tripterygium wilfordii* Hook. f. as raw material was refluxed with 95% ethanol for 342 h, wherein the ratio of 95% ethanol to dried rhizome of *Tripterygium wilfordii* is 4-16:1;
   b) the extractive solution from step a) was concentrated under reduced pressure to obtain crude extract, and the crude extract was adsorbed on neutral alumina;
   c) the crude extract on neutral alumina in step b) was extracted with trichloromethane, and the trichloromethane extractive solution was concentrated under reduced pressure to obtain *tripterygium* glycosides;
   d) the *tripterygium* glycosides obtained in step c) was heated in a buffer solution prepared by sodium dihydrogen phosphate and phosphoric acid with pH of 3.0-5.0, and refluxed for hydrolysis reaction for 18-96 h in an oil bath at 90-120° C.;
   e) sampling the amount of triptolide before and after the reaction in step d), to calculate the reduction amount of triptolide before and after the reaction in step d);

f) adding triptriolide-anhydrous ethanol solution to the reaction product in step d), mixing, evaporating the solvent, and obtaining low toxic *tripterygium* neoglycosides, wherein the addition amount of triptriolide triptriolide-anhydrous ethanol solution is >0 to 20 times of the reduction amount of triptolide in molar.

* * * * *